United States Patent [19]

Hayashi et al.

[11] 4,070,537
[45] Jan. 24, 1978

[54] 17-OXO-17-PHENYL-PROSTAGLANDINS

[75] Inventors: Masaki Hayashi; Seiji Kori, both of Takatsuki; Hajimu Miyake, Suita; Kimiichiro Matsumoto, Takatsuki, all of Japan

[73] Assignee: Ono Pharmaceutical Company, Osaka, Japan

[21] Appl. No.: 679,299

[22] Filed: Apr. 22, 1976

[30] Foreign Application Priority Data

May 30, 1975 United Kingdom ............... 18039/75
Oct. 20, 1975 United Kingdom ............... 43041/75

[51] Int. Cl.² ............................................. C07C 69/76
[52] U.S. Cl. ................................ 560/51; 260/343.3 P; 260/346.2; 260/514 D; 560/121; 424/308
[58] Field of Search .................... 260/473 R, 520 R

[56] References Cited

FOREIGN PATENT DOCUMENTS 2,605,584  2/1975  Germany ......................... 260/473 R Primary Examiner—Paul J. Killos
Attorney, Agent, or Firm—Albert H. Graddis; Frank S. Chow

[57] ABSTRACT

The present invention relates to 17-oxo-17-phenyl-prostaglandins having the following structural formula:

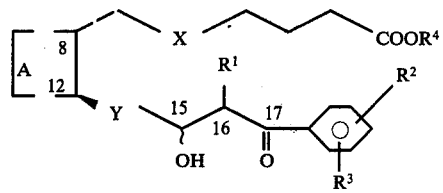

(VI)

wherein A represents a grouping of the formula:

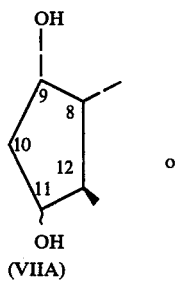

or 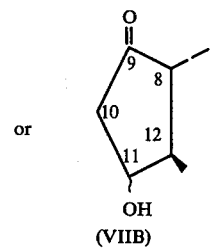

(VIIA) (VIIB)

X represents ethylene or cis-vinylene, Y represents ethylene or trans-vinylene, $R^1$ represents a hydrogen atom or a methyl or ethyl group, $R^2$ and $R^3$, which may be the same or different, each represent a hydrogen or halogen atom, a trifluoromethyl group or a straight- or branched-chain alkyl group containing from 1 to 3 carbon atoms, and $R^4$ represents a hydrogen atom or a straight- or branched-chain alkyl group containing from 1 to 12 carbon atoms and cyclodextrin clathrates of such acids and esters, and when $R^4$ represents a hydrogen atom, non-toxic salts thereof.

These compounds exhibit characteristic prostaglandin activity, e.g., abortifacient activity, stimulation activity on uterine contraction, and so on.

6 Claims, No Drawings

17-OXO-17-PHENYL-PROSTAGLANDINS

This invention relates to new prostaglandin analogues, to a process for their preparation and to pharmaceutical compositions containing them.

Prostaglandins are derivatives of prostanoic acid which has the following formula:

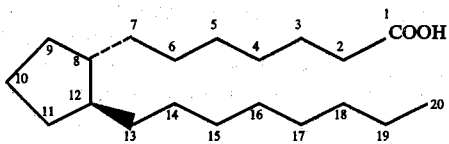 (I)

Various types of prostaglandins are known, the types depending inter alia on the structure and substituents on the alicyclic ring. For example, the alicyclic rings of prostaglandins F(PGF) and E(PGE) have the structures:

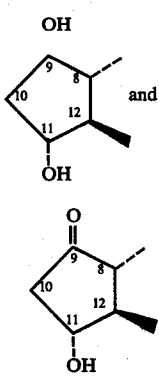

respectively. The dotted lines in the foregoing formulae and in other formulae throughout this specification denote, in accordance with generally accepted rules of nomenclature, that the attached grouping lies behind the general plane of the ring system, i.e. that the grouping is in α-configuration, that the thickened lines denote that the grouping lies in front of the general plane of the system, i.e. that the grouping is in β-configuration, and that the wavy line indicates that the grouping is in α- or β-configuration.

Such compounds are sub-classified according to the position of double bond(s) in the side chain(s) attached to the 8- and 12-positions of the alicyclic ring. Thus $PG_1$ compounds have a trans-double bond between $C_{13}$-$C_{14}$(trans-$\Delta^{13}$) and $PG_2$ compounds have a cis-double bond between $C_5$-$C_6$ and a trans-double bond between $C_{13}$-$C_{14}$(cis-$\Delta^5$, trans-$\Delta^{13}$). For example, prostaglandin $F_{1\alpha}$($PGF_{1\alpha}$) and prostaglandin $E_1$ ($PGE_1$) are characterized by the following structures IV and V:

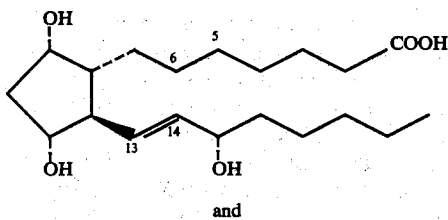

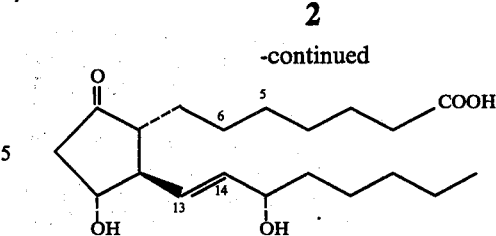

respectively. The structures of $PGF_{2\alpha}$ and $PGE_2$, as members of the $PG_2$ group, correspond to those of formulae IV and V respectively with a cis-double bond between the carbon atoms in positions 5 and 6. Compounds in which the double bond between the carbon atoms in positions 13 and 14 of members of the $PG_1$ group is replaced by ethylene (—$CH_2CH_2$—) are known as dihydroprostaglandins, e.g. dihydro-prostaglandin-$F_{1\alpha}$ (dihydro-$PGF_{1\alpha}$) and dihydro-prostaglandin-$E_1$ (dihydro-$PGE_1$).

Moreover, when one or more methylene groups are added to, or eliminated from, the aliphatic group attached to the 12-position of the alicyclic ring of the prostaglandins the compounds are known, in accordance with the usual rules of organic nomenclature, as homoprostaglandins (methylene group added) or nor-prostaglandins (methylene group eliminated) and, when more than one methylene group is added or eliminated, the number is indicated by di-, tri- etc. before the prefix "homo" or "nor".

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGEs have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia. $PGE_1$ inhibits blood platelet aggregation and also removes the thrombus and prevents thrombosis. PGEs and PGFs have a stimulating effect on smooth muscle and increase the intestinal peristalsis; these actions indicate therapeutic utility on post-operative ileus and as purgatives. Furthermore, PGEs and PGFs may be used as oxytocics, as abortifacients in the first and second trimesters; in the post-labour abortion of the placenta, and as oral contraceptives because they regulate the sexual cycle of female mammals. PGEs have vasodilator and diuretic activities and are useful for improvement in patients suffering from cerebral vascular disease because they increase the cerebral blood flow, and are also useful in the treatment of asthmatic conditions in patients because of their bronchodilating activity.

During the past decade widespread investigations have been carried out in order to discover inter alia new products possessing the pharmacological properties of the 'natural' prostaglandins or one or more of such properties to an enhanced degree, or hitherto unknown pharmacological properties. It has now been found that by replacing the hydrogen atoms attached to the 17-position of the aliphatic group attached to the 12-position of the alicyclic ring of prostaglandins E and F by the oxo radical and by replacing the propyl group attached to the 17-position by an optionally substituted phenyl group the pharmacological properties of the 'natural' prostaglandins are, in some aspects of their activities, improved or modified.

The present invention accordingly provides new prostaglandin analogues of the general formula:

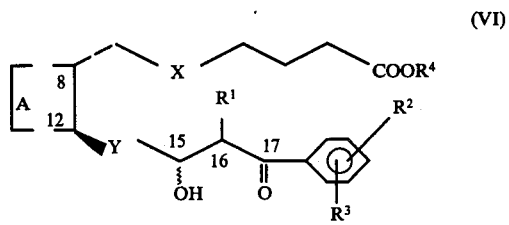

[wherein A represents a grouping of the formula:

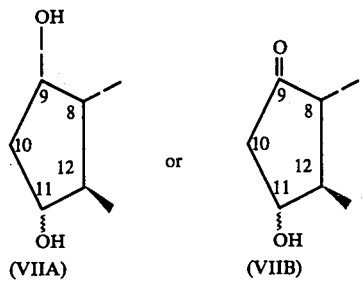

X represents ethylene (i.e. —CH$_2$CH$_2$—) or, preferably, cis-vinylene (i.e. —CH=CH—), Y represents ethylene or, preferably, trans-vinylene, R$^1$ represents a methyl or ethyl group or, preferably, a hydrogen atom, R$^2$ and R$^3$, which may be the same or different, each represent a hydrogen atom, a halogen (preferably chlorine) atom, a trifluoromethyl group or a straight- or branched-chain alkyl group containing from 1 to 3 carbon atoms, R$^2$ preferably representing a hydrogen or chlorine atom and R$^3$ preferably representing a hydrogen atom, and R$^4$ represents a hydrogen atom or a straight- or branched-chain alkyl group containing from 1 to 12 carbon atoms (preferably methyl)] and cyclodextrin clathrates of such acids and esters and, when R$^4$ represents a hydrogen atom, non-toxic salts thereof. Compounds of general formula VI wherein the hydroxy group attached to the 15-position is in the α-configuration are preferred, and more particularly those such compounds wherein the hydroxy group depicted in formulae VIIA and VIIB in α- or β-configuration is attached to the 11-position carbon atom in the α-configuration.

The present invention is concerned with all compounds of general formula VI in the 'natural' form or its enantiomeric form, or mixtures thereof, more particularly the racemic form consisting of equimolecular mixtures of natural and its enantiomeric form.

As will be apparent to those skilled in the art, the compounds depicted in general formula VI have at least three centres of chirality, these three centres of chirality being at the alicyclic ring carbon atoms of group A identified as 8 and 12 and at the C-15 carbon atom which has attached to it a hydroxy group. Still further centres of chirality occur when the alicyclic group A carries a hydroxy group on the carbon atom in position 11 (i.e. when the ring is that of formula VIIB) or hydroxy groups in positions 9 and 11 (i.e. when the ring is that of formula VIIA) and a further centre of chirality occurs at the C-16 carbon atom when the symbol R$^1$ represents a methyl or ethyl group. The presence of chirality leads, as is well known, to the existence of isomerism. However, the compounds of general formula VI all have such a configuration that the side-chains attached to the ring carbon atoms in the positions identified as 8 and 12 are trans with respect to each other. Accordingly, all isomers of general formula VI, and mixtures thereof, which have those side-chains attached to the ring carbon atoms in positions 8 and 12 in the trans-configuration and have a hydroxy group as depicted in the 15-position are to be considered within the scope of general formula VI.

According to a feature of the present invention, the prostaglandin analogues of general formula VI, wherein the various symbols are as hereinbefore defined, are prepared by the process which comprises reacting a cyclopentane derivative of the general formula:

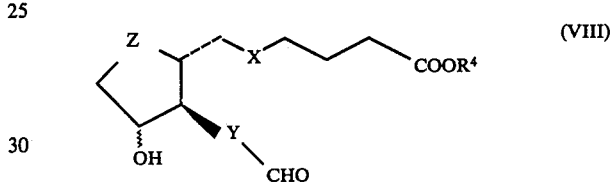

(wherein X, Y and R$^4$ are as hereinbefore defined, and Z represents

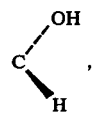

or C=O) with an organo-lithium compound of the general formula:

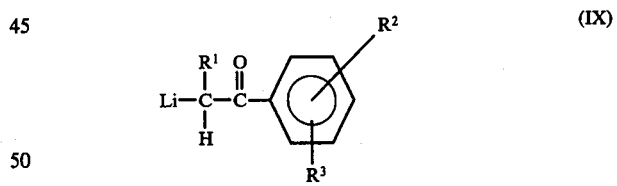

(wherein R$^1$, R$^2$ and R$^3$ are as hereinbefore defined), and hydrolyzing the resulting organo-lithium complex to obtain a mixture of the 15α- and 15β-hydroxy epimers of general formula VI, and optionally separating the 15α-hydroxy isomer from the 15β-hydroxy isomer.

The reaction of a compound of general formula VIII with a compound of general formula IX is preferably effected at a lower temperature, and preferably below −50° C., in an inert organic solvent, e.g. diethyl ether, tetrahydrofuran, 1,2-dimethoxyethane or n-hexane, for a period of from 10 minutes to 3 hours. The reaction mixture is then hydrolysed by treatment with water or an aqueous solution of an acid, e.g. acetic acid or oxalic acid, or ammonium chloride to give a mixture of the 15α- and 15β-hydroxy epimers of general formula VI. It is sometimes possible to separate the 15α-hydroxy isomer from the 15β-hydroxy isomer by column chromatography on silica gel.
Compounds of general formula VIII, wherein the hydroxy group in the 11-position is in the α-configuration and the other symbols are as hereinbefore defined, may be prepared by the sequence of reactions hereinafter depicted schematically in Scheme A:
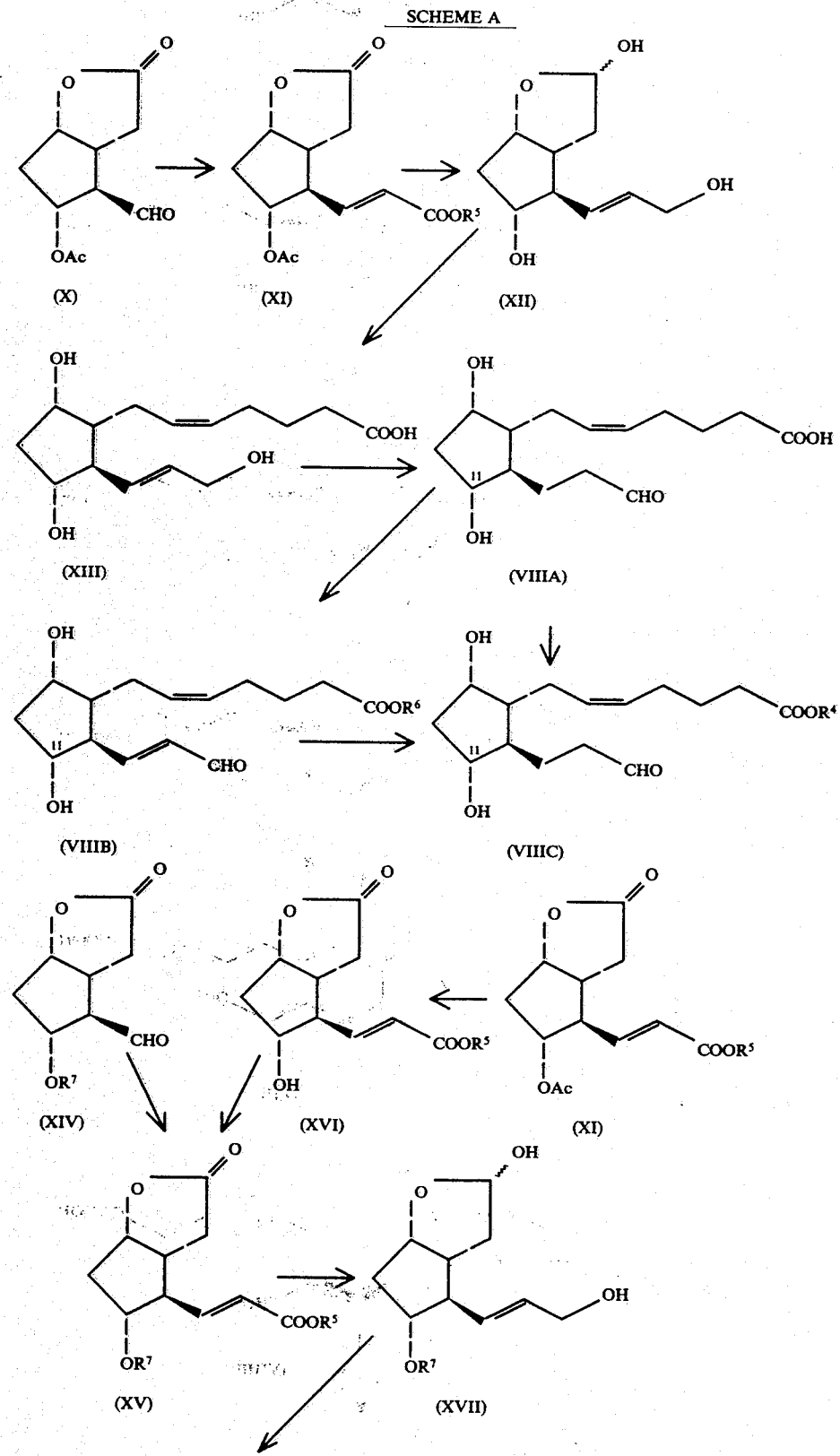

4,070,537
SCHEME A -continued
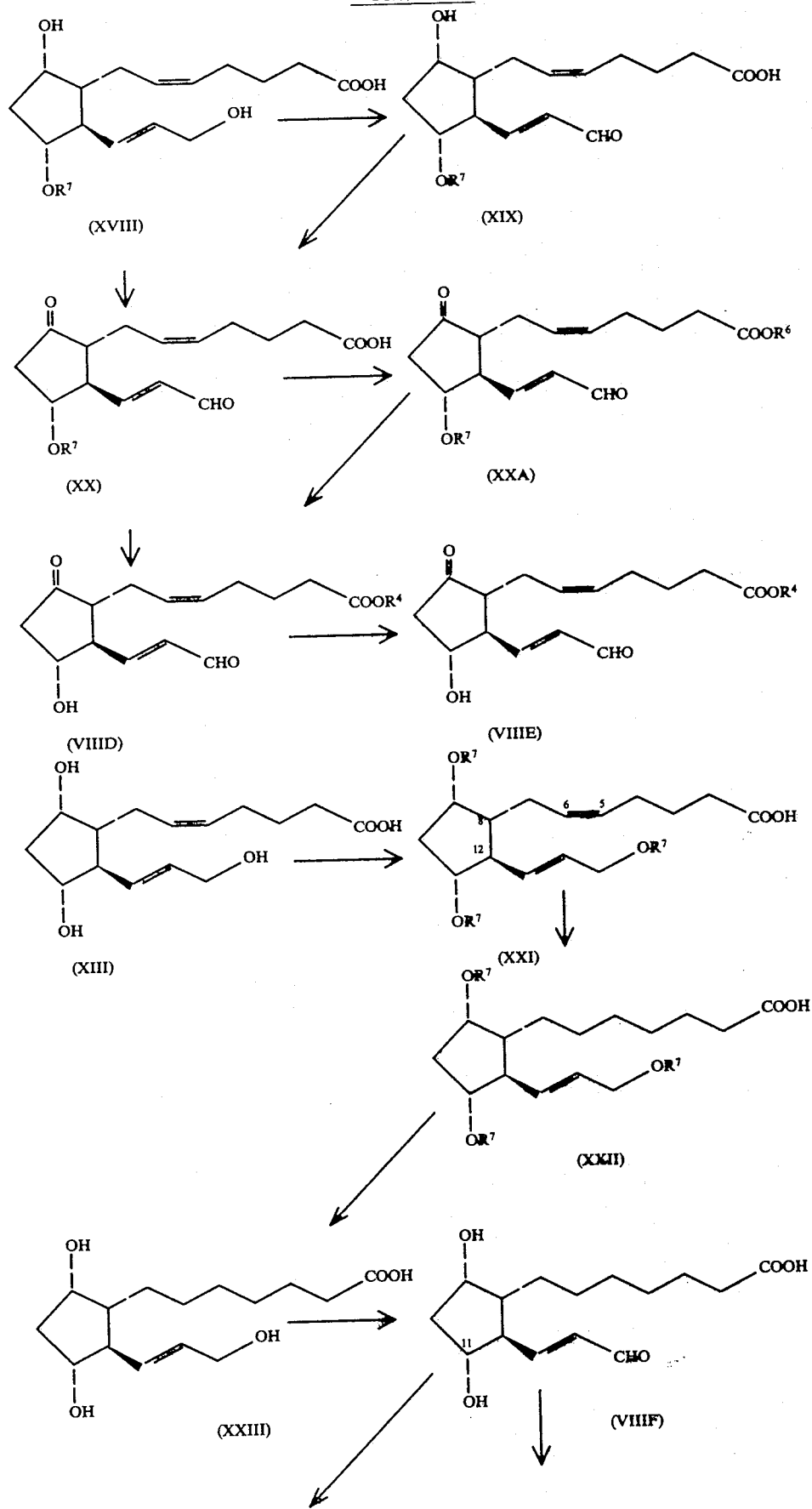

-continued
SCHEME A
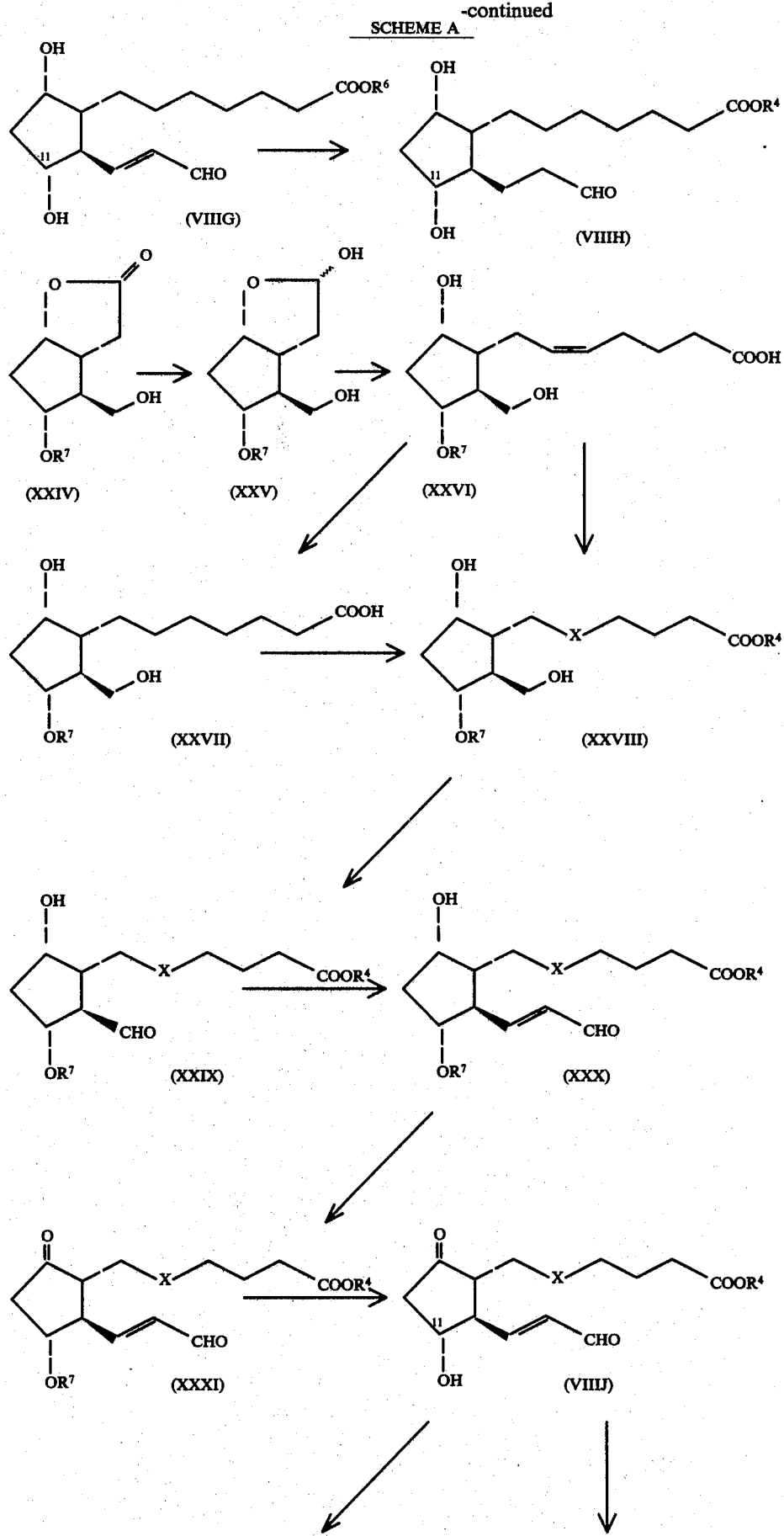

SCHEME A -continued

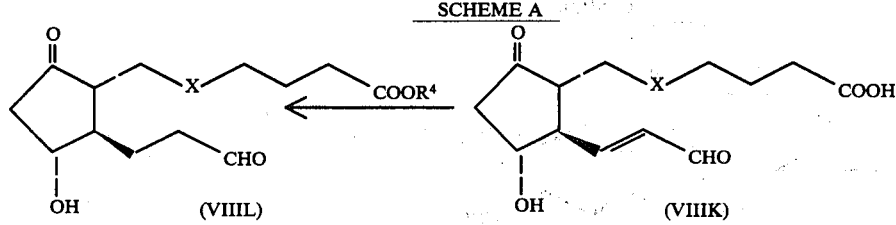

wherein X and $R^4$ are as hereinbefore defined, Ac represents the acetyl group, $R^5$ represents a straight- or branched-chain alkyl group containing from 1 to 4 carbon atoms, $R^6$ represents a straight- or branched-chain alkyl group containing from 1 to 12 carbon atoms, and $R^7$ represents a 2-tetrahydropyranyl group unsubstituted or substituted by at least one alkyl group, a 2-tetrahydrofuranyl group or a 1-ethoxyethyl group.

The starting compound of formula X is prepared according to the method described in J. Amer. Chem. Soc., 91, 5675 (1969) and J. Amer. Chem. Soc., 92, 397 (1970) and may be converted stereoselectively in high yield to the trans-α,β-unsaturated esters of general formula XI by reaction with the sodio derivative of a compound of the general formula:

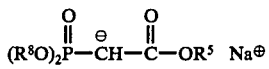

(wherein $R^5$ is as hereinbefore defined, and $R^8$ represents a straight- or branched-chain alkyl group containing from 1 to 4 carbon atoms) in an inert organic solvent, e.g. tetrahydrofuran or 1,2-dimethoxyethane, at a temperature of from 0° to 30° C., the reaction usually being complete in two hours.

The compounds of general formula XI may be converted quantitatively to compounds of formula XII by reduction with more than 4 equivalents of diisobutylaluminium hydride in an inert organic solvent, e.g. toluene, n-pentane or n-hexane, at a low temperature, e.g. −78° to −20° C. Reduction of an α,β-unsaturated ester with diisobutylaluminium hydride has not been previously described in the literature and, furthermore, it has not been previously known that the reduction of an α,β-unsaturated ester with diisobutylaluminium hydride gives an allylic alcohol, and not an aldehyde.

A compound of formula XIII may be prepared by the reaction of a compound of formula XII with a compound of the formula:

in the presence of a strong base, for example sodium methylsulphinylmethylide under the normal conditions utilized for effecting the Wittig reaction, e.g. in an inert organic solvent, at ambient temperature. The reaction is preferably carried out in dimethyl sulphoxide because the compound of formula XXXIII is practically insoluble in other solvents, e.g. tetrahydrofuran, and because a cis-double bond must be formed stereospecifically in the Wittig reaction. For the better performance of the Wittig reaction, more than three equivalents of the phosphorane compound, prepared from the compound of formula XXXIII, viz. (4-carboxybutylidene)triphenylphosphorane, are required. Reaction between the compound of formula XII and the phosphorane is usually completed in about one to five hours at laboratory temperature. The products of formula XIII, i.e. the acid component of the reaction mixture, may be isolated from the reaction mixture in a high yield by conventional procedures.

Compounds of formula XIII may be converted into compound of formula VIIIA by oxidation with manganese dioxide, for example in an inert organic solvent, e.g. acetone, at laboratory temperature, which oxidises an allylic alcohol group selectively to a formyl group.

Compounds of formula VIIIA may be converted into compounds of general formula VIIIB by known methods, for example by reaction with (a) appropriate diazoalkane compounds, e.g. diazomethane, (b) appropriate alcohols in the presence of N,N'-dicyclohexylcarbodiimide as a condensing agent, or (c) appropriate alcohols following the formation of a mixed acid anhydride by adding a tertiary amine and then a pivaloyl halide or an arylsulphonyl or alkylsulphonyl halide (cf. our British Pat. Nos. 1362956 and 1364125). By the term "known methods" as used in this specification is meant methods heretofore used or described in the chemical literature.

Compounds of general formulae VIIIA and VIIIB may, if desired, be converted to compounds of general formula VIIIC by the selective reduction of the carbonyl conjugated double bond of the compounds of general formula VIIIA and VIIIB by known methods, for example by means of lithium-1-pentyne-hydrocuprate (LiCuH-C≡C-n-C$_3$H$_7$) [see J. Amer. Chem. Soc. 96, 3686 (1974)].

Compounds of general formula XIV may be converted stereoselectively to trans-α,β-unsaturated esters of general formula XV by the application of the procedure hereinbefore described for the conversion of compounds of formula X into the trans-α,β-unsaturated esters of general formula XI. Compounds of general formula XV can also be prepared from compounds of general formula XI by selective deacetylation with an equimolar amount of anhydrous potassium carbonate in absolute methanol and then etherification of the compounds of general formula XVI thus obtained with a dihydropyran, dihydrofuran or ethylvinyl ether in an inert organic solvent, e.g. methylene chloride, in the presence of a condensing agent, for example p-toluenesulphonic acid.

Compounds of general formula XV may be converted to compounds of general formula XVII quantitatively by reduction with more than 3 molar equivalents of diisobutylaluminium hydride in an inert organic solvent, e.g. toluene, n-hexane or n-pentane, at a low temperature, e.g. at −78° to −20° C.

Compounds of general formula XVII may be converted to compounds of general formula XVIII by the methods hereinbefore described for the preparation of a compound of formula XIII from a compound of formula XII.

Compounds of general formula XVIII may be converted into compounds of general formula XIX by selective oxidation with manganese dioxide, for example in an inert organic solvent, e.g. acetone or methylene chloride, at laboratory temperature, which oxidizes an allylic alcohol group to a formyl group.

Compounds of general formula XIX may be converted into compounds of general formula XX by oxidation under mild and neutral conditions, e.g. with Collins' reagent or Jones' reagent at a moderately low temperature, e.g. below room temperature.

The compounds of general formula XX can also be prepared from compounds of general formula XVIII by oxidation under mild and neutral conditions, e.g. with Collins' reagent or Jones' reagent at a moderately low temperature, e.g. below room temperature.

Compounds of general formula XX may be esterified to obtained compounds of general formula XXA by known methods as hereinbefore described for the esterification of a compound of formula VIIIA.

Compounds of general formula XX and XXA may be converted to compounds of general formula VIIID by mild hydrolysis with an aqueous solution of an organic acid, e.g. acetic acid, or with a dilute aqueous inorganic acid, e.g. hydrochloric acid, advantageously in the presence of an organic solvent miscible with water, e.g. tetrahydrofuran or an alkanol containing from 1 to 4 carbon atoms, e.g. methanol, at a temperature ranging from ambient to 60° C., preferably below 45° C.

Compounds of general formula VIIID may be converted to compounds of general formula VIIIE by selective reduction of the carbonyl conjugated double bond of compounds of general formula VIID by known methods, for example by means of lithium 1-pentynehydrocuprate.

Compounds of formula XIII may be converted into compounds of general formula XXI by the application of the procedure hereinbefore described for the etherification of compounds of general formula XVI to give compounds of general formula XV.

Compounds of general formula XXII may be prepared by reduction of the vinylene group in the $C_5$-$C_6$ position of compounds of general formula XXI by hydrogenation in the presence of a hydrogenation catalyst, for example palladium black or palladium on charcoal, in the presence of an inert organic solvent, for example, a lower alkanol, e.g. methanol or ethanol, at laboratory temperature and at normal pressure, the hydrogenation being monitored to avoid reduction of the vinylene group in the side-chain attached to the 12-position of the cyclopentane ring.

Compounds of general formula XXII may be converted to compounds of formula XXIII by mild hydrolysis with an aqueous solution of an organic acid, e.g. acetic acid, or with a dilute aqueous solution of an inorganic acid, e.g. hydrochloric acid, advantageously in the presence of an organic solvent miscible with water, e.g. tetrahydrofuran or an alkanol, at a temperature ranging from ambient to 60° C. and preferably below 45° C.

Compounds of formula XXIII may be converted to compounds of formula VIIIF by the application of the procedure hereinbefore described for the conversion of compounds of formula XIII to compounds of formula VIIIA.

Compounds of formula VIIIF may be converted into compounds of general formula VIIIG by the application of the procedures hereinbefore described for the conversion of compounds of formula VIIIA to compounds of general formula VIIIB.

Compounds of general formula VIIIF and VIIIG may, if desired, by converted to compounds of general formula VIIIH by selective reduction of the carbonyl conjugated double bond of the compounds of general formula VIIIF and VIIIG by known methods, for example by means of lithium 1-pentyne-hydrocuprate.

Compounds of general formula XXIV may be converted to compounds of general formula XXV by reduction with diisobutylaluminium hydride in an inert organic solvent, e.g. toluene, n-hexane or n-pentane, at a low temperature, e.g. at −78° to −20° C.

Compounds of general formula XXV may be converted to compounds of general formula XXVI by the application of the procedures hereinbefore described for the conversion of compounds of the general formula XII into compounds of the general formula XIII.

Compounds of general formula XXVI may, if desired, be converted to compounds of general formula XXVII. Suitably the reduction may be effected by hydrogenation in the presence of a hydrogenation catalyst, for example palladium on charcoal, palladium black or platinum dioxide, in the presence of an inert organic solvent, for example a lower alkanol, e.g. methanol or ethanol, at laboratory temperature and at normal or elevated pressure, e.g. at a hydrogen pressure from atmospheric to 15 kilogrammes per square centimetre.

Compounds of general formula XXVI and XXVII may, if desired, be converted to compounds of general formula XXVIII by known methods, for example by reacting with (a) appropriate diazoalkane compounds, e.g. diazomethane, (b) appropriate alcohols in the presence of N,N'-dicyclohexylcarbodiimide as a condensing agent, or (c) appropriate alcohols following the formation of a mixed acid anhydride by adding a tertiary amine and then a pivaloyl halide or an arysulphonyl or alkylsulphonyl halide (cf. our British Pat. Nos. 1362956 and 1364125).

Compounds of general formula XXVIII may be converted to compounds of general formula XXIX by reaction with a chromium trioxide-pyridine complex in an inert organic solvent, e.g. methylene chloride, at a low temperature, preferably at 0° C.

Compounds of general formula XXIX may be converted to compounds of general formula XXX by reaction with formylmethylenetriphenylphosphorane of formula $(C_6H_5)_3P=CHCHO$ [a known compound described in J. Chem. Soc., 1266 (1961) by S. Tripett and D. M. Walker] in an inert organic solvent, e.g. benzene, dimethylformamide or dimethyl sulphoxide, at a temperature ranging from 30° to 80° C.

Compounds of general formula XXX may be converted to compounds of general formula XXXI by the application of the procedures hereinbefore described for the conversion of compounds of general formula XIX into compounds of the general formula XX.

Compounds of general formula XXXI may be converted to compounds of general formula VIIIJ by the application of the procedures hereinbefore described for the conversion of compounds of general formula XXII into compounds of general formula XXIII.

Compounds of general formula VIIIJ may, if desired, be converted to compounds of general formula VIIIK by treatment with bakers yeast [cf. C. J. Sih et al, J. Amer. Chem. Soc., 94, 3643 (1972)].

Compounds of general formula VIIIJ and VIIIK may, if desired, be converted to compounds of general formula VIIIL by the selective reduction of the carbonyl conjugated double bond of compounds of general formula VIIIJ and VIIIK by methods known per se, for example by means of lithium 1-pentyne-hydrocuprate.

Compounds of general formula XIV and XXIV may be prepared by the sequence of reactions depicted schematically in Scheme B:

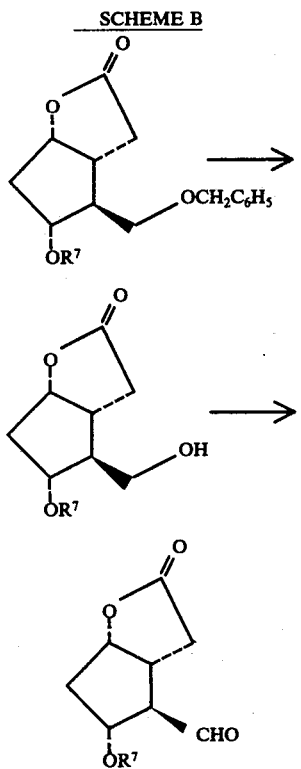

(wherein $R^7$ is as hereinbefore defined). Compounds of general formula XXIV may be prepared from compounds of general formula XXXIV by catalytic reduction in the presence of a hydrogenation catalyst, for example palladium on charcoal or palladium black, and converted to compounds of general formula XIV by oxidation under mild conditions, e.g. with Collins' reagent and at a moderately low temperature.

Compounds of general formula XXXIV may be prepared by known methods, for example as described in J. Org. Chem. 37, 2921 (1972) for the preparation of the compound of general formula XXXIV wherein $R^7$ is a 2-tetrahydropyranyl group.

Compounds of general formula VIII corresponding to compounds of general formulae VIIIA, VIIIB, VIIIC, VIIID, VIIIE, VIIIF, VIIIG and VIIIH wherein the hydroxy group in the 11-position is in the 62-configuration instead of the α-configuration and the other symbols are as hereinbefore defined, which may be used as starting materials to prepare prostaglandin analogues of general formula VI, may be prepared by the series of reactions depicted in Scheme A but replacing the compounds of formula X by the compounds of the formula:

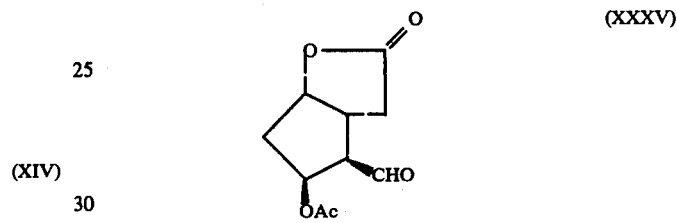

wherein Ac is as hereinbefore defined.

A method for the preparation of the bicyclooctane starting materials of formula XXXV, wherein Ac is as hereinbefore defined, utilizing known procedures may be represented by the series of reactions depicted schematically below in Scheme C (cf. E. J. Corey and Shiro Terashima, Tetrahedron Letters, No. 2, pp. 111–113, 1972):

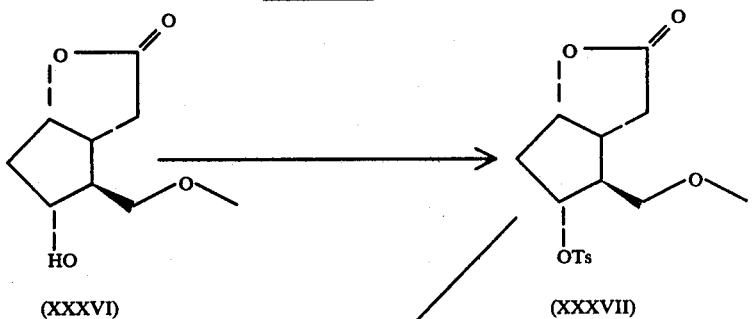

SCHEME C

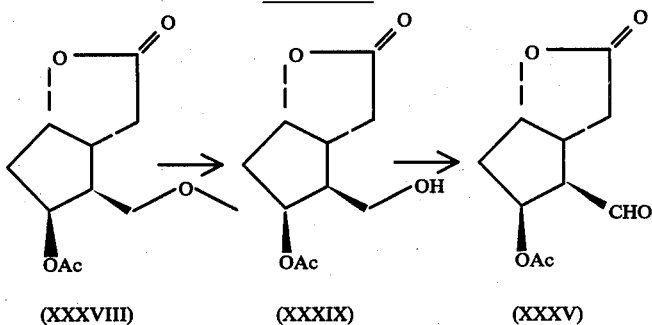

(XXXVIII)  (XXXIX)  (XXXV)

wherein Ac is as hereinbefore defined and Ts represents the tosyl group. The various reactions depicted above in Scheme C may be effected by known methods. Compounds of formula XXXVIII may be prepared by reacting compounds of formula XXXVII with tetraethylammonium acetate. Compounds of formula XXXIX may be converted to compounds of formula XXXV by oxidation under mild conditions, e.g. with Collins' reagent and at a moderately low temperature.

Compounds corresponding to those of general formula VIIID and VIIIE wherein the hydroxy group in the 11-position is in the β-configuration instead of the α-configuration and the other symbols are as hereinbefore defined, may also be prepared by the series of reactions depicted in Scheme A but replacing the compounds of formula XIV by compounds of the general formula:

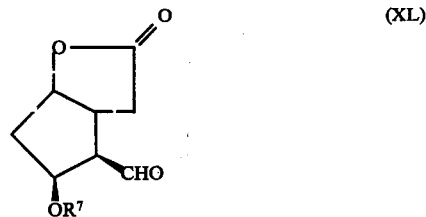

(XL)

wherein $R^7$ is as hereinbefore defined.

Compounds of the general formula XL wherein $R^7$ is as hereinbefore defined may be prepared by the series of reactions depicted schematically below in Scheme D:

SCHEME D

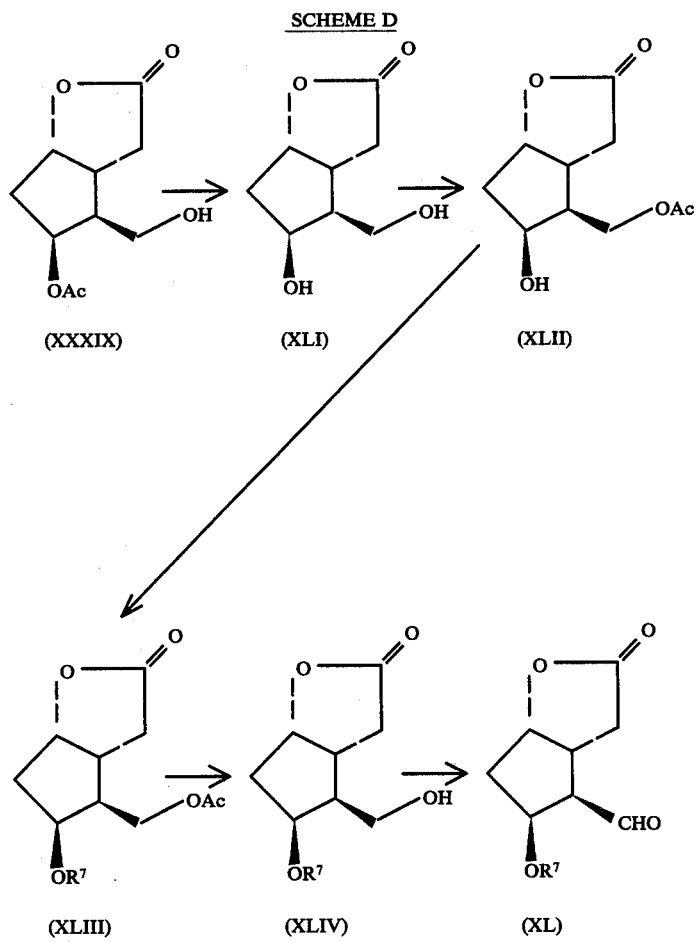

(XXXIX)  (XLI)  (XLII)

(XLIII)  (XLIV)  (XL)

wherein $R^7$ and Ac are as hereinbefore defined. The various reactions depicted above in Scheme D may be effected by known methods. Compounds of formula XLII may be prepared by selective acetylation of compounds of formula XLI under mild conditions, for example, with an equimolecular amount of acetyl chloride at a low temperature, for example, $-20°$ to $-10°$ C.

Compounds of general formula VIII corresponding to compounds of general formulae VIIIJ, VIIIK and VIIIL wherein the hydroxy group in the 11-position is in the $\beta$-configuration instead of the $\alpha$-configuration and the other symbols are as hereinbefore defined, which may be used as starting materials to prepare prostaglandin analogues of general formula VI, may be prepared by the series of reactions depicted in Scheme A but replacing the compounds of formula XXIV by compounds of general formula XLIV.

Compounds of general formula IX may be obtained by reacting a compound of general formula:

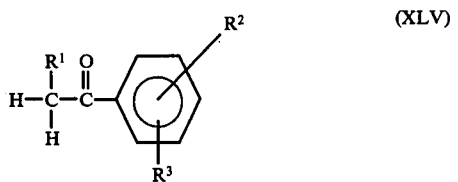

(XLV)

(wherein $R^1$, $R^2$ and $R^3$ are as hereinbefore defined) with lithium diisopropylamide, which is prepared by reacting diisopropylamine with an alkyllithium, e.g. n-butyllithium, in an inert organic solvent, e.g. n-hexane or tetrahydrofuran, at a low temperature, e.g. $-20°$ C.

Compounds of general formula XLV may be prepared from an acid of the general formula:

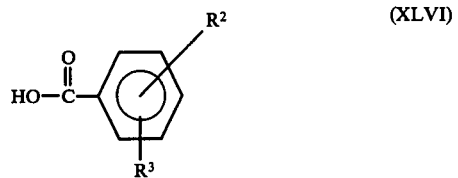

(XLVI)

(wherein $R^2$ and $R^3$ are as hereinbefore defined) by reaction with an alkyllithium $R^9$-Li (wherein $R^9$ represents a methyl, ethyl or n-propyl group) in an inert organic solvent, e.g. tetrahydrofuran or diethyl ether, at a low temperature, e.g. 0° to 30° C.

The prostaglandin analogues of general formula VI wherein $R^4$ represents a hydrogen atom may, if desired, be converted by methods known per se into salts.

The salts may be prepared, for example, by reaction of stoichiometric quantities of an acid of general formula VI and the appropriate base, e.g. an alkali metal hydroxide or carbonate, ammonium hydroxide or carbonate, ammonia or an amine, in a suitable solvent. The salts may be isolated by lyophilisation of the solution or, if sufficiently insoluble in the reaction medium, by filtration, if necessary after removal of part of the solvent. Preferably the salts are non-toxic salts, i.e. salts the cations of which are relatively innocuous to the animal organism when used in therapeutic doses so that the beneficial pharmacological properties of the prostaglandins of general formula VI are not vitiated by side-effects ascribable to those cations. Preferably the salts are water-soluble. Suitable salts include the alkali metal, e.g. sodium and potassium, and ammonium salts and pharmaceutically-acceptable (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms.

The prostaglandins of general formula VI may, if desired, be converted into cyclodextrin clathrates. The clathrates may be prepared by dissolving the cyclodextrin in water and/or an organic solvent which is miscible with water and adding to the solution the prostaglandin compound in a water-miscible organic solvent. The mixture is then heated and the desired cyclodextrin clathrate product isolated by concentrating the mixture under reduced pressure or by cooling and separating the product by filtration or decanting. The ratio of organic solvent to water may be varied according to the solubilities of the starting materials and products. Preferably the temperature is not allowed to exceed 70° C. during the preparation of the cyclodextrin clathrates. $\alpha$, $\beta$ or $\gamma$-Cyclodextrins or mixtures thereof may be used in the preparation of the cyclodextrin clathrates. Conversion into their cyclodextrin clathrates serves to increase the stability of the prostaglandin compounds.

The prostaglandin analogues of general formula VI and their cyclodextrin clathrates and, when $R^4$ represents a hydrogen atom, non-toxic salts possess the valuable pharmacological properties typical of the prostaglandins in a selective fashion, including, in particular, abortifacient activity and stimulatory activity on uterine contraction, luteolytic and antinidatory activity and inhibitory activity on gastric acid secretion and gastric ulceration and are useful in the termination of pregnancy and induction of labour in pregnant female mammals, in the treatment of impaired fertility, in the control of oestrus, contraception and menstrual regulation in female mammals, and in the treatment of gastric ulceration. For example, in standard laboratory tests, (i) 17-oxo-17-phenyl-18,19,20-trinor-PGF$_{2\alpha}$ methyl ester, 17-oxo-17-phenyl-18,19,20-trinor-PGE$_2$ methyl ester, 17-oxo-17-(3-chlorophenyl)-18,19,20-trinor-PGF$_{2\alpha}$ methyl ester, 17-oxo-17-(4-chlorophenyl)-18,19,20-trinor-PGF$_{2\alpha}$ methyl ester, 17-oxo-17-(4-chlorophenyl)-18,19,20-trinor-PGF$_{2\alpha}$ and 17-oxo-17-(3-chlorophenyl)-18,19,20-trinor-PGF$_{2\alpha}$ stimulate uterine contraction in the pregnant female rat when administered intravenously on the 20th day of gestation at doses of 20, 10, 10, 20, 50 and 20–50 $\mu$g./kg. animal body weight, respectively, (ii) 17-oxo-17-phenyl-18,19,20-trinor-PGF$_{2\alpha}$ methyl ester, 17-oxo-17-(3-chlorophenyl)-18,19,20-trinor-PGF$_{2\alpha}$ methyl ester, 17-oxo-17-(4-chlorophenyl)-18,19,20-trinor-PGF$_{2\alpha}$ methyl ester, 17-oxo-17-(4-chlorophenyl)-18,19,20-trinor-PGF$_{2\alpha}$ and 17-oxo-17-(3-chlorophenyl)-18,19,20-trinor-PGF$_{2\alpha}$ inhibit implantation in pregnant female rats when administered subcutaneously on the 3rd, 4th and 5th days of pregnancy at daily doses of 0.02 to 0.5, 0.2, 0.5, 1.0 and 0.5 mg./kg. animal body weight, respectively, and (iii) in stress ulceration of rats [produced according to the method of Takagi and Okabe - Jap. J. Pharmac. 10, 9–18 (1968) by soaking rats in a water bath at 19° C. for 6 hours], 17-oxo-17-phenyl-18,19,20-trinor-PGE$_2$ methyl ester produces 59.6% and 73.9% inhibitions of stress ulceration by oral administration at doses of 1 and 2 mg./kg. animal body weight, respectively.

The following Reference Examples and Examples illustrate the preparation of new prostaglandin analogues of the present invention. In them 'IR', 'NMR' and 'TLC' represent respectively 'Infrared absorption spectrum', 'Nuclear magnetic resonance spectrum' and 'Thin layer chromatography'.

REFERENCE EXAMPLE 1

2α-(6-Methoxycarbonylhex-cis-2-enyl)-3β-(2-formyleth-trans-1-enyl)-cyclopentan-1α,4α-diol A solution of freshly prepared diazomethane in diethyl ether was added to a solution of 1.0 g. of 2α-(6-carboxyhex-cis-2-enyl)-3β-(2-formyleth-trans-1-enyl)-cyclopentan-1α,4α-diol in 100 ml. of ethyl acetate at 0° C. and the mixture was stirred at the same temperature for 10 minutes. The reaction mixture was concentrated under reduced pressure and the residue was purified by column chromatography on silica gel using a mixture of benzene and ethyl acetate (1:2) as eluent to give 820 mg. of 2α-(6-methoxycarbonylhex-cis-2-enyl)-3β-(2-formyleth-trans-1-enyl)-cyclopentan-1α,4α-diol having the following physical characteristics:

NMR (CDCl$_3$ solution): δ; 3.66 (3H, s), 4.00–4.32 (2H, m), 5.25–5.55 (2H, m), 6.17 (1H, d-d), 6.78 (1H, d-d), 9.51 (1H, d);

IR (liquid film): ν; 3400, 1730, 1690, 1630, 980 cm$^{-1}$.

2α-(6-Carboxyhex-cis-2-enyl)-3β-(2-formyleth-trans-1-enyl)-cyclopentan-1α,4α-diol, used as a starting material in the procedure described above, was prepared as follows:

Under an atmosphere of nitrogen and at laboratory temperature, 140 ml. of absolute methylene chloride and 16.1 ml. of absolute pyridine were stirred with 10 g. of chromium trioxide for 30 minutes. 20 g. of infusorial earth were then added to the solution. After cooling the temperature to 0° C., 2.14 g. of 2-oxa-3-oxo-6-syn-hydroxymethyl-7-anti-acetoxy-cis-bicyclo[3,3,0]octane [prepared as described in J. Amer. Chem. Soc., 92 397 (1970)] in 20 ml. of methylene chloride were then added and the mixture was stirred for 15 minutes at 0° C. The reaction mixture was then treated with 25 g. of sodium bisulphate and stirred for a further 10 minutes at 0° C. and filtered through a pad of magnesium sulphate. The filtrate was then concentrated under reduced pressure below 0° C. to give 2-oxa-3-oxo-6-syn-formyl-7-anti-acetoxy-cis-bicyclo[3,3,0]octane.

369 mg. of sodium hydride (65% content) were suspended in 60 ml. of absolute tetrahydrofuran. With stirring under an atmosphere of nitrogen at room temperature, 1.82 g. of trimethyl phosphonoacetate [prepared as described in C.R. Acad, Sci. Paris. Ser. A,B 262B 515 (1966)] were added to the suspension, and the mixture was stirred for 30 minutes.

The formyl compound (obtained as described above) in 30 ml. of tetrahydrofuran, was added, whilst maintaining the temperature below 15° C., and the mixture was stirred for 2 hours at 15° C. Then the reaction mixture was treated with 2 ml. of acetic acid to pH 5 and concentrated slightly. The product was treated with 20 ml. of water and extracted twice with 80 ml. of ethyl acetate (total volume 160 ml.). The organic layer was washed with an aqueous solution of sodium chloride, dried over magnesium sulphate and concentrated under reduced pressure. The residue was purified by column chromatography on silica gel using a mixture of ethyl acetate-benzene (1:4) as eluent to give 2.0 g. of 2-oxa-3-oxo-6-syn-(2-methoxycarbonyleth-trans-1-enyl)-7-anti-acetoxy-cis-bicyclo[3,3,0]octane having the following physical characteristics:

IR (liquid film): ν; 2970, 1775, 1735, 1710, 1650, 1240, 1160, 1037 and 980 cm$^{-1}$;

NMR (CDCl$_3$ solution): δ; 6.77 (1H, d), 5.87 (1H, d), 5.00 (2H, m), 3.70 (3H, s), 3.0–1.9 (6H, m), 2.04 (3H, s);

TLC (developing solvent, ethyl acetate - benzene = 1:2); Rf = 0.38.

28 g. of 2-oxa-3-oxo-6-syn-(2-methoxycarbonyleth-trans-1-enyl)-7-anti-acetoxy-cis-bicyclo[3,3,0]octane (prepared by the procedure described above) were dissolved in 1.6 liters of toluene and the solution cooled to −55° C. To that solution, 340 ml. of a 25% (w/v) solution of diisobutylaluminium hydride in toluene were added and the mixture was stirred at −40° C. for 20 minutes. Methanol was then added to the reaction mixture in order to decompose excess diisobutylaluminium hydride, and then water was added to the reaction mixture. The precipitate was filtered off and washed thoroughly with ethanol. The filtrate and the washings were combined and concentrated under reduced pressure to dryness. The residue was washed with acetone to give 13.3 g. of 2-oxa-3-hydroxy-6-syn-(3-hydroxyprop-trans-1-enyl)-7-anti-hydroxy-cis-bicyclo[3,3,0]octane as a white powder having the following physical characteristics:

m.p.; 131.5° to 132.5° C.;

IR (KBr tablet): ν; 3370, 3250, 990 and 950 cm$^{-1}$;

NMR (dimethyl sulphoxide-d$_6$ solution): δ; 5.98 (1H, d), 5.65–5.30 (3H, m), 4.90–4.50 (2H, m), 4.50–4.20 (1H, m), 3.96 (2H, m) and 3.80–3.40 (1H, m);

TLC (developing solvent, methylene chloride - methanol = 9:1); Rf = 0.17.

1.84 g. of sodium hydride (65% content) were suspended in 25 ml. of dimethyl sulphoxide and the suspension was stirred with heating at 65° C. for 40 minutes to obtain sodium methylsulphinylmethylide. The reaction mixture was allowed to cool to room temperature and then added dropwise to a solution of 11.1 g. of (4-carboxybutyl)triphenylphosphonium bromide in 16 ml. of dimethyl sulphoxide, the reaction temperature being kept at 25° C.

A solution of 1.0 g. of 2-oxa-3-hydroxy-6-syn-(3-hydroxyprop-trans-1-enyl)-7-anti-hydroxy-cis-bicyclo[3,3,0]octane in 15 ml. of dimethyl sulphoxide was added, and the mixture stirred vigorously at 25° C. for 30 minutes and then at 40° C. for 45 minutes. The reaction mixture was poured into 250 ml. of ice-water and neutral substance were removed by extraction with ethyl acetate. The aqueous layer was acidified with oxalic acid to pH 3 to 4 and extracted thoroughly with ethyl acetate. The extracts were concentrated under reduced pressure. In the course of the concentration, the resulting precipitate was filtered off. The residue was purified by column chromatography on silica gel using a mixture of chloroform - tetrahydrofuran (5:1) and then a mixture of ethyl acetate - ethanol (30:1) as eluents to give 840 mg. of 2α-(6-carboxyhex-cis-2-enyl)-3β-(3-hydroxyprop-trans-1-enyl)-cyclopentan-1α,4α-diol as an oil having the following physical characteristics:

IR (liquid film): ν; 3400, 1710, 980 and 760 cm$^{-1}$;

NMR (CDCl$_3$ - dimethyl sulphoxide-d$_6$ solution): δ; 5.90–4.80 (8H, m), 4.20–3.75 (4H, m), 2.50–1.75 (8H, m), and 1.75–1.30 (4H, m);

TLC (developing solvent, methylene chloride - methanol = 4:1); Rf = 0.30.

6 g. of active manganese dioxide were added to a solution of 334 mg. of 2α-(6-carboxyhex-cis-2-enyl)-3β-(3-hydroxyprop-trans-1-enyl)-cyclopentan-1α,4α-diol in 60 ml. of acetone and the mixture was stirred at room temperature for 25 hours. The precipitate was filtered off, washed with acetone thoroughly, and the filtrate and the washings were combined and concentrated under reduced pressure.

The residue was purified by column chromatography on silica gel using ethyl acetate as eluent to give 188 mg. of 2α-(6-carboxyhex-cis-2-enyl)-3β-(2-formyleth-trans-1-enyl)-cyclopentan-1α,4α-diol having the following physical characteristics:

IR (liquid film): ν; 3400, 1720-1680 and 980 cm$^{-1}$;

NMR (CDCl$_3$ - dimethyl sulphoxide-d$_6$ solution): δ; 9.52 (1H, d), 6.82 (1H, d-d), 6.17 (1H, d-d), 6.00-4.50 (5H, m), 4.25-3.90 (2H, m) and 3.55-2.85 (1H, m);

TLC (developing solvent, ethyl acetate - formic acid = 400:5); Rf = 0.21.

EXAMPLE 1

17-Oxo-17-phenyl-18, 19, 20-trinor-PGF$_{2α}$ methyl ester 10 ml. of a 1.2M solution of n-butyllithium in n-hexane were added dropwise to a solution of 1.68 ml. of diisopropylamine in 10 ml. of dry tetrahydrofuran at −20° C. under an atmosphere of nitrogen. After stirring for 30 minutes, a solution of 1.2 ml. of acetophenone in 3 ml. of tetrahydrofuran was added to the reaction mixture and the mixture was stirred for 30 minutes to obtain a solution of ω-lithium-acetophenone [described in Chem. Ber., 102, 1944 (1969)].

The solution thus obtained was added dropwise at −78° C. to a solution of 915 mg. of 2α-(6-methoxy-carbonylhex-cis-2-enyl)-3β-(2-formyleth-trans-1-enyl)-cyclopentan-1α,4α-diol (prepared as described in Reference Example 1) in 30 ml. of tetrahydrofuran and the reaction mixture was stirred at that temperature for a further one hour, neutralized with 2 ml. of acetic acid and extracted with ethyl acetate. The organic extracts were washed with an aqueous oxalic acid solution, water, an aqueous sodium bicarbonate solution and an aqueous sodium chloride solution, dried over sodium sulphate and concentrated under reduced pressure. The residue was purified by column chromatography on silica gel using a mixture of cyclohexane and ethyl acetate (2:3) as eluent to give 439 mg. of the title compound and 424 mg. of its 15β-hydroxy isomer. The title compound showed the following physical characteristics:

TLC (developing solvent ethyl acetate): Rf = 0.21; (15β-hydroxy isomer : Rf = 0.31);

IR (liquid film): ν; 3400, 3060, 3000, 2930, 1740, 1685, 1600, 1585, 1450, 980, 760, 700 cm$^{-1}$;

NMR (CDCl$_3$ solution): δ; 8.10-7.80 (2H, m), 7.75-7.30 (3H, m), 5.80-5.54 (2H, m), 5.54-5.15 (2H, m), 4.90-4.55 (1H, m), 4.35-3.80 (2H, m), 3.66 (3H, s), 3.22 (2H, d);

Optical Rotation: [α]$_D^{20}$ = +9.3° (c = 1.6, CHCl$_3$).

REFERENCE EXAMPLE 2

2α-(6-Methoxycarbonylhex-cis-2-enyl)-3β-(2-formyleth-trans-1-enyl)-4α-hydroxy-cyclopentan-1-one 1.0 g. of 2α-(6-carboxyhex-cis-2-enyl)-3β-(3-hydroxyprop-trans-1-enyl)-4α-(2-tetrahydropyranyloxy)-cyclopentan-1α-ol was dissolved in 47.5 ml. of diethyl ether and the solution was cooled to 0° C. 47.5 ml. of a chromic acid solution (prepared by dissolving 12 g. of manganese sulphate, 2.5 g. of chromium trioxide and 2.75 ml. of sulphuric acid in 50 ml. of water) were added and the reaction mixture was stirred vigorously for one hour at −5° to 5° C. The reaction mixture was extracted with diethyl ether after saturation with sodium sulphate of the aqueous layer. The ethereal extract was washed with water and with a saturated aqueous sodium chloride solution, dried over magnesium sulphate and concentrated under reduced pressure. The residue was purified by column chromatography on silica gel using a mixture of benzene and ethyl acetate (2:1) as eluent to give 250 mg. of 2α-(6-carboxyhex-cis-2-enyl)-3β-(2-formyleth-trans-1-enyl)-4α-(2-tetrahydropyranyloxy)-cyclopentan-1-one having the following physical characteristics:

NMR (CDCl$_3$ solution): δ; 2.5-3.0 (1H, d-d), 4.5-4.8 (1H, m), 5.0-5.6 (2H, m), 6.25 (1H, d-d), 6.90 (1H, d-d), 7.3-7.8 (1H, m), 9.62 (1H, d);

IR (liquid film): ν; 3000, 2930, 2850, 1735, 1685, 1435, 1345, 1155, 1125, 1075, 1035, 975, 915 cm$^{-1}$;

TLC (developing solvent, benzene - ethyl acetate = 1:2); Rf = 0.60.

2.0 g. of 2α-(6-carboxyhex-cis-2-enyl)-3β-(2-formyleth-trans-1enyl)-4α-(2-tetrahydropyranyloxy)-cyclopentan-1-one (prepared as described above) were dissolved in 200 ml. of diethyl ether and to this solution there was added a solution of freshly prepared diazomethane in diethyl ether at 0° C. After stirring at the same temperature for 10 minutes, the reaction mixture was concentrated under reduced pressure and the residue was purified by column chromatography on silica gel using a mixture of benzene and ethyl acetate (3:1) as eluent to give 1.65 g. of 2α-(6-methoxycarbonylhex-cis-2-enyl)-3β-(2-formyleth-trans-1-enyl)-4α-(2-tetrahydropyranyloxy)-cyclopentan-1-one having the following physical characteristics:

NMR (CDCl$_3$ solution): δ; 3.63 (3H, s), 4.5-4.8 (1H, m), 5.05-5.7 (2H, m), 6.25 (1H, d-d), 6.93 (1H, d-d), 7.59 (1H, d);

IR (liquid film): ν; 2940, 2860, 1740, 1690, 1640, 1440, 1350, 1250, 1200, 1080, 1035, 975 cm$^{-1}$.

1.46 g. of 2α-(6-methoxycarbonylhex-cis-2-enyl)-3β-(2-formyleth-trans-1-enyl)-4α-(2-tetrahydropyranyloxy)-cyclopentan-1-one (prepared as described above) were dissolved in 44 ml. of a mixture of acetic acid, water and tetrahydrofuran (65:35:10) and the solution was stirred at 38° to 40° C. for 3.5 hours. The reaction mixture was then diluted with 200 ml. of ethyl acetate, washed with water and with a saturated aqueous sodium chloride solution, dried over magnesium sulphate and concentrated under reduced pressure. The residue was purified by column chromatography on silica gel using a mixture of benzene and ethyl acetate (1:1) as eluent to give 1.02 g. of 2α-(6-methoxycarbonylhex-cis-2-enyl)-3β-(2-formyleth-trans-1-enyl)-4α-hydroxy-cyclopentan-1-one having the following physical characteristics:

NMR (CDCl$_3$ solution): δ; 3.72 (3H, s), 4.34 (1H, q), 5.2-5.7 (2H, m), 6.20 (1H, d-d), 6.84 (1H, d-d), 9.45 (1H, d);

TLC (developing solvent, methylene chloride - methanol = 20:1); Rf = 0.32.

2α-(6-Carboxyhex-cis-2-enyl)-3β-(3-hydroxyprop-trans-1-enyl)-4α-(2-tetrahydropyranyloxy)-cyclopentan-1α-ol, used as a starting material in the procedure described above, was prepared as follows:

2.68 g. of 2-oxa-3-oxo-6-syn-(2-methoxycarbonyleth-trans-1-enyl)-7-anti-acetoxy-cis-bicyclo[3,3,0]octane (prepared as described in Reference Example 1) in 30 ml. of absolute methanol and 1.38 g. of potassium carbonate were stirred at room temperature for 15 minutes, successively cooled in an ice-bath and neutralized with 20 ml. of 1N hydrochloric acid. 260 ml. of ethyl acetate and 27 ml. of an aqueous solution of sodium bicarbonate were added to the reaction mixture and the mixture was separated into two layers. The organic layer was washed with an aqueous solution of sodium chloride, dried over magnesium sulphate and concentrated under reduced pressure to give 1.96 g. of 2-oxa-3-oxo-6-syn-(2-methoxycarbonyleth-trans-1-enyl)-7-anti-hydroxy-cis-bicyclo[3,3,0]octane having the following physical characteristics:

IR (liquid film): $\nu$; 3430, 1786-1690 (broad) and 1650 cm$^{-1}$;

NMR (CDCl$_3$ solution): $\delta$; 6.82 (1H, dd), 5.90 (1H, d), 4.95 (1H, m), 3.72 (3H, s), 4.30-3.25 (2H, m) and 2.90-1.70 (6H, m);

TLC (developing solvent, methylene chloride - methanol = 19:1); Rf = 0.38.

2.31 g. of 2-oxa-3-oxo-6-syn-(2-methoxycarbonyleth-trans-1-enyl)-7-anti-hydroxy-cis-bicyclo[3,3,0]octane (prepared by the procedure described above) were dissolved in 30 ml. of methylene chloride and the solution was stirred with 20 mg. of p-toluenesulphonic acid and 3 ml of dihydropyran for 15 minutes at room temperature. The reaction mixture was neutralized with an aqueous solution of sodium bicarbonate, diluted with ethyl acetate, washed with an aqueous solution of sodium chloride, dried over magnesium sulphate and concentrated under reduced pressure. The residue was purified by column chromatography on silica gel using a mixture of ethyl acetate - benzene (1:3) as eluent to give 3.0 g. of 2-oxa-3-oxo-6-syn-(2-methoxycarbonyleth-trans-1-enyl)-7-anti-(2-tetrahydropyranyloxy)-cis-bicyclo[3,3,0]octane as white crystals having the following physical characteristics:

m.p.; 85° C.;

IR (KBr tablet): $\nu$; 2930, 1770, 1710, 1650, 1343, 1240, and 1152 cm$^{-1}$;

NMR (CDCl$_3$ solution): $\delta$; 6.78 (1H, dd), 5.84 (1H, d), 4.97 (1H, m), 4.63 (1H, m), 3.71 (3H, s) and 4.30-3.20 (3H, m);

TLC (developing solvent, ethyl acetate - benzene = 1:2); Rf = 0.34.

3.10 g. of 2-oxa-3-oxo-6-syn-(2-methoxycarbonyleth-trans-1-enyl)-7-anti-(2-tetrahydropyranyloxy)-cis-bicyclo[3,3,0]octane (prepared by the procedure described above) were dissolved in 100 ml. of toluene and the solution was cooled to −65° C. To the solution, 23 ml. of a 25% (w/v) solution of diisobutylaluminium hydride in toluene were added and the mixture was stirred for 20 minutes at −60° C. Methanol was then added to decompose excess diisobutylaluminium hydride together with water. The precipitate was filtered off and the filtrate was dried and concentrated under reduced pressure to give 2.8 g. of 2-oxa-3-hydroxy-6-syn-(3-hydroxyprop-trans-1-enyl)-7-anti-(2-tetrahydropyranyloxy)-cis-bicyclo[3,3,0]octane having the following physical characteristics:

IR (liquid film): $\nu$; 3390, 2930, 1350 and 1120 cm$^{-1}$;

NMR (CDCl$_3$ solution): $\delta$; 5.75-5.15 (3H, m) and 4.75-3.34 (8H, m);

TLC (developing solvent, methylene chloride - methanol = 19:1); Rf = 0.23.

2.94 g. of sodium hydride (65% content) were suspended in 40 ml. of dimethyl sulphoxide and stirred with heating at 65° C. for 40 minutes to obtain sodium methylsulphinylmethylide. The reaction mixture was allowed to cool to room temperature and then added dropwise to a solution of 18.5 g. of (4-carboxybutyl)-triphenylphosphonium bromide in 40 ml. of dimethyl sulphoxide, the reaction temperature being kept within the range of 20° to 25° C.

A solution of 2.84 g. of 2-oxa-3-hydroxy-6-syn-(3-hydroxyprop-trans-1enyl)-7-anti-(2-tetrahydropyranyloxy)-cis-bicyclo[3,3,0]octane (obtained by the procedure described above) in 40 ml. of dimethyl sulphoxide was added, and the mixture stirred vigorously at 25° C. for 1 hour. The reaction mixture was then poured into 500 ml. of ice-water and neutral substances were removed by extraction with a mixture of ethyl acetate and diethyl ether (1:1). The aqueous layer was acidified to pH 3 with a saturated solution of oxalic acid and extracted with a mixture of diethyl ether and ethyl acetate (1:1). The extracts, after washing with water, were dried over magnesium sulphate and concentrated under reduced pressure to give crude 2α-(6-carboxyhex-cis-2-enyl)-3β-(3-hydroxyprop-trans-1-enyl)-4α-(2-tetrahydropyranyloxy)-cyclopentan-1α-ol having the following physical characteristics:

IR (liquid film): $\nu$; 2930, 1720, 1240 and 1120 cm$^{-1}$;

NMR (CDCl$_3$ solution): $\delta$; 5.70-5.25 (4H, m) and 4.62 (1H, m);

TLC (developing solvent, methylene chloride - methanol = 19:1); Rf = 0.23.

EXAMPLE 2

17-Oxo-17-phenyl-18, 19, 20-trinor-PGE$_2$ methyl ester 13 ml. of the solution of ω-lithium-acetophenone (prepared as described in Example 1) were added dropwise at −78° C., under an atmosphere of nitrogen, to a solution of 800 mg. of 2α-(6-methoxycarbonylhex-cis-2-enyl)-3β-(2-formyleth-trans-1-enyl)-4α-hydroxy-cyclopentan-1-one (prepared as described in Reference Example 2) in 20 ml. of tetrahydrofuran and the reaction mixture was stirred at that temperature for a further one hour, neutralized with 2 ml. of acetic acid and extracted with ethyl acetate. The organic extracts were washed with an aqueous oxalic acid solution, water, an aqueous sodium bicarbonate solution and an aqueous sodium chloride solution, dried over sodium sulphate and concentrated under reduced pressure. The residue was purified by column chromatography on silica gel using a mixture of cyclohexane and ethyl acetate (1:1) as eluent to give 424 mg. of the title compound and 426 mg. of its 15β-hydroxy isomer. The title compound showed the following physical characteristics:

TLC (developing solvent, ethyl acetate); Rf = 0.30; (15β-hydroxy isomer : Rf = 0.37);

IR (liquid film): $\nu$; 3430, 3060, 3000, 2950, 2900, 1745, 1685, 1600, 1585, 1450, 1370, 1165, 1080, 980, 760, 700 cm$^{-1}$;

NMR (CDCl$_3$ solution): $\delta$; 8.10-7.80 (2H, m), 7.73-7.30 (3H, m), 5.90-5.57 (2H, m), 5.57-5.10 (2H, m), 4.95-4.60 (1H, m), 4.30-3.90 (3H, m), 3.64 (3H, s), 3.23 (2H, d), 2.90-2.55 (1H, dd);

Optical Rotation: $[\alpha]_D^{20}$ = −97.1° (c = 1.2, CHCl$_3$).

EXAMPLE 3

17-Oxo-17-(4-chlorophenyl)-18,19,20-trinor-PGF$_{2\alpha}$ methyl ester 4 ml. of a 1.4M solution of n-butyllithium in n-hexane were added dropwise to a solution of 0.95 ml. of diisopropylamine in 10 ml. of dry tetrahydrofuran at −20°

C. under an atmosphere of nitrogen. After stirring for 20 minutes, a solution of 0.596 ml. of 4-chlorophenyl methyl ketone in 2 ml. of tetrahydrofuran was added, and the reaction mixture was stirred for 20 minutes. The reaction mixture thus obtained was added dropwise at −78° C. to a solution of 400 mg. of 2α-(6-methoxycarbonylhex-cis-2-enyl)-3β-(2-formyleth-trans-1-enyl)-cyclopentan-1α,4α-diol (prepared as described in Reference Example 1) in 3 ml. of tetrahydrofuran and the reaction mixture was stirred at that temperature for 1 hour and 15 minutes, quenched with acetic acid and extracted with ethyl acetate. The organic extracts were washed with an aqueous solution of sodium chloride, dried over magnesium sulphate and concentrated under reduced pressure. The residue was purified by column chromatography on silica gel using mixtures of ethyl acetate and cyclohexane (1:1 and 2:1) as eluents to give 150 mg. of the title compound and 157 mg. of its 15β-hydroxy isomer. The title compound showed the following physical characteristics:

TLC (developing solvent ethyl acetate): Rf = 0.28, (15β-hydroxy isomer: Rf = 0.42);

IR (liquid film): ν; 3400, 3000, 2940, 1730, 1680, 1590, 1430, 1400, 1110, 770 cm$^{-1}$;

NMR (CDCl$_3$ solution): δ; 7.9 (2H, d), 7.43 (2H, d), 5.85-5.14 (4H, m), 4.95-4.55 (1H, m), 4.3-3.8 (2H, m), 3.65 (3H, s), 3.3-3.05 (2H, m).

EXAMPLE 4

17-Oxo-17-(3-chlorophenyl)-18,19,20-trinor-PGF$_{2α}$ methyl ester 5.15 ml. of a 1.4M solution of n-butyllithium in n-hexane were added dropwise to a solution of 1.22 ml. of diisopropylamine in 10 ml. of dry tetrahydrofuran at −20° C. under an atmosphere of nitrogen. After stirring for 20 minutes, a solution of 0.76 ml. of 3-chlorophenyl methyl ketone (prepared as described hereinafter) in 3 ml. of tetrahydrofuran was added, and the reaction mixture was stirred for 20 minutes. The reaction mixture thus obtained was added dropwise at −78° C. to a solution of 440 mg. of 2α-(6-methoxycarbonylhex-cis-2-enyl)-3β-(2-formyleth-trans-1-enyl)-cyclopentan-1α,-4α-diol (prepared as described in Reference Example 1) in 5 ml. of tetrahydrofuran and the reaction mixture was stirred at that temperature for 2 hours, quenched with acetic acid and extracted with ethyl acetate. The organic extracts were washed with an aqueous solution of sodium chloride, dried over magnesium sulphate and concentrated under reduced pressure. The residue was purified by column chromatography on silica gel using mixtures of cyclohexane and ethyl acetate (5:4 and 1:2) as eluents to give 163 mg. of the title compound and 173 mg. of its 15β-hydroxy isomer. The title compound showed the following physical characteristics:

TLC (developing solvent ethyl acetate): Rf = 0.30, (15β-hydroxy isomer: Rf = 0.44);

IR (liquid film): ν; 3400, 3000, 2925, 1740, 1680, 1570, 1430, 790 cm$^{-1}$;

NMR (CDCl$_3$ solution): δ; 8.0-7.25 (4H, m), 5.8-5.15 (4H, m), 4.9-4.55 (1H, m), 4.3-3.78 (2H, m), 3.64 (3H, s), 3.3-3.05 (2H, m).

3-Chlorophenyl methyl ketone, used in the procedure described above, was prepared as follows:

4.5 g. of 3-chlorobenzoic acid were dissolved in 50 ml. of dry tetrahydrofuran. The solution was cooled to 0° C., and 22.2 ml. of a 1.3M solution of methyllithium in diethyl ether was added dropwise over 10 minutes, with stirring under an atmosphere of nitrogen. After stirring for 15 minutes, the reaction mixture was allowed to return to room temperature, and 22.2 ml. of methyllithium reagent was added at that temperature over 40 minutes. After stirring for 15 minutes, crushed ice was added to the reaction mixture and the mixture was stirred for 5 minutes. The reaction mixture was then extracted with diethyl ether, washed with an aqueous solution of sodium chloride, dried over magnesium sulphate and concentrated under reduced pressure. The residue was purified by distillation in vacuo to give 3.4 g. of 3-chlorophenyl methyl ketone having the following physical characteristics:

boiling point: 118° to 119° C./20 mm. Hg;

TLC (developing solvent ethyl acetate): Rf = 0.83;

IR (liquid film): ν; 3500, 3060, 1685, 1570, 1420, 1360, 1250, 1080, 795 cm$^{-1}$.

EXAMPLE 5

17-Oxo-17-(4-chlorophenyl)-18,19,20-trinor-PGF$_{2α}$ 9.65 ml. of a 1.4M solution of n-butyllithium in n-hexane were added dropwise to a solution of 2.3 ml. of diisopropylamine in 20 ml. of dry tetrahydrofuran at −20° C. under an atmosphere of nitrogen. After stirring for 20 minutes, a solution of 1.48 ml. of 4-chlorophenyl methyl ketone (prepared by a procedure similar to that described in Example 4 in respect of 3-chlorophenyl methylketone) in 5 ml. of tetrahydrofuran was added and the reaction mixture was stirred for 20 minutes. The reaction mixture thus obtained was added dropwise at −78° C. to a solution of 700 mg. of 2α-(6-carboxyhex-cis-2-enyl)-3β-(2-formyleth-trans-1-enyl)-cyclopentan-1α,4α-diol (prepared as described in Reference Example 1) in 10 ml. of tetrahydrofuran and the reaction mixture was stirred for 1.5 hours, quenched with acetic acid, diluted with ice-water and extracted with ethyl acetate. The organic extracts were washed with an aqueous solution of sodium chloride, dried over magnesium sulphate and concentrated under reduced pressure. The residue was purified by column chromatography on silica gel using a mixture of ethyl acetate and cyclohexane (3:1) followed by ethyl acetate alone as eluents to give 153 mg. of the title compound and 149 mg. of its 15β-hydroxy isomer. The title compound showed the following physical characteristics:

TLC (developing solvent ethyl acetate - formic acid = 400:5): Rf = 0.415, (15β-hydroxy isomer: Rf = 0.45);

IR (liquid film): ν; 3400, 3050, 2950, 1710, 1680, 1400, 1095, 970 cm$^{-1}$;

NMR (acetone-d$_6$ solution): δ; 8.03 (2H, d), 7.54 (2H, d), 5.95-5.1 (4H, m), 5.0-3.5 (9H, m), 3.4-3.05 (2H, m).

EXAMPLE 6

17-Oxo-17-(3-chlorophenyl)-18,19,20-trinor-PGF$_{2α}$ 10 ml. of a 1.4M solution of n-butyllithium in n-hexane were added dropwise to a solution of 2.48 ml. of diisopropylamine in 20 ml. of dry tetrahydrofuran at −20° C. under an atmosphere of nitrogen. After stirring for 20 minutes, a solution of 1.6 ml. of 3-chlorophenyl methyl ketone (prepared as described in Example 4) in 5 ml. of tetrahydrofuran was added and the reaction mixture was stirred for 20 minutes. The reaction mixture thus obtained was added dropwise at −78° C. to a solution of 800 mg. of 2α-(6-carboxyhex-cis-2-enyl)-3β-(2-formyleth-trans-1-enyl)-cyclopentan-1α,4α-diol (prepared as described in Reference Example 1) in 10 ml. of tetrahydrofuran and the reaction mixture was stirred at that temperature for one hour, quenched with acetic acid, diluted with ice-water and extracted with ethyl acetate. The organic extracts were washed with an aqueous solution of sodium chloride, dried over magnesium sulphate and concentrated under reduced pressure. The residue was purified by column chromatography on silica gel using a mixture of ethyl acetate and cyclohexane (7:4) followed by ethyl acetate alone as eluents to give 140 mg. of the title compound and 131 mg. of its 15β-hydroxy isomer. The title compound showed the following physical characteristics:

TLC (developing solvent ethyl acetate - formic acid = 400:5); Rf = 0.35, (15β-hydroxy isomer: Rf = 0.37);

IR (liquid film): ν; 3400, 3010, 2950, 1710, 1680, 1590, 1570, 1420, 965 cm$^{-1}$;

NMR (acetone-d$_6$ solution): δ; 8.1-7.8 (2H, m), 7.8-7.45 (2H, m), 5.8-5.1 (4H, m), 4.9-4.1 (9H, m), 3.35-3.05 (2H, m).

The present invention includes within its scope pharmaceutical compositions which comprise at least one pharmacologically active prostaglandin analogues of general formula VI or a cyclodextrin clathrate or, when R$^4$ represents a hydrogen atom, a non-toxic salt thereof, together with a pharmaceutical carrier or coating. In clinical practice such novel compounds will normally be administered orally, rectally, vaginally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, mannitol or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention for oral administration also include capsules of absorbable material such as gelatin containing one or more of the active substances with or without the addition of diluents or excipients.

Solid compositions for rectal administration include suppositories formulated in manner known per se and containing one or more of the active compounds.

Solid compositions for vaginal administration include pessaries formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the adult, the doses per person are generally between 0.5 and 100 μg. by oral administration in the treatment of gastric ulceration and, in the case of female mammals, between 0.001 and 50 mg. by oral, intravaginal, intravenous and extra-amniotic administration for contraception and menstrual regulation in female mammals and in the termination of pregnancy and the induction of labour in pregnant female mammals. In domestic female mammals such as cows, mares, sows, ewes and bitches, the doses are generally between 0.001 and 50 mg./animal by intramuscular, subcutaneous, intrauterine, intravaginal and intravenous administration for the synchronisation of oestrus and treatment of impaired fertility.

The following Example illustrates pharmaceutical compositions according to the invention.

EXAMPLE 7

17-Oxo-17-(3-chlorophenyl-18,19,20-trinor-PGF$_{2\alpha}$ methyl ester (2 mg.) was dissolved in ethanol (10 ml.), mixed with mannitol (18.5 g.), sieved through a 30-mesh sieve, dried at 30° C. for 90 minutes and again sieved through a 30-mesh sieve. Aerosil (microfine silica; 200 mg.) was added and the powder obtained was machine-filled into one hundred No. 2 hard gelatin capsules to give capsules each containing 20 μg. of 17-oxo-17-(3-chlorophenyl)-18,19,20-trinor-PGF$_{2\alpha}$ methyl ester which after swallowing of the capsule is released into the stomach.

We claim:

1. A compound of the formula:

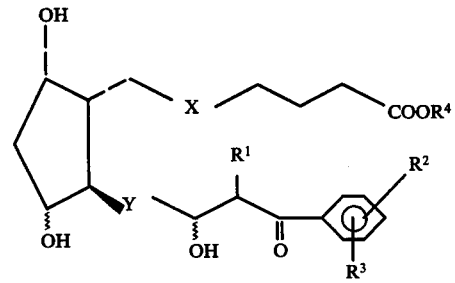

VI wherein X represents ethylene or cis-vinylene, Y represents ethylene or trans-vinylene, R$^1$ represents a hydrogen atom or a methyl or ethyl group, R$^2$ and R$^3$, which may be the same or different, each represent a hydrogen or halogen atom, a trifluoromethyl group or a straight- or branched-chain alkyl group containing from 1 to 3 carbon atoms, and R$^4$ represents a hydrogen atom or a straight- or branched-chain alkyl group containing from 1 to 12 carbon atoms and cyclodextrin clathrates of such acids and esters, and when $R^4$ represents a hydrogen atom, non-toxic salts thereof.

2. A compound according to claim 1 which is 17-oxo-17-phenyl-18,19,20-trinor-PGF$_{2\alpha}$ methyl ester.

3. A compound according to claim 1 which is 17-oxo-17-(4-chlorophenyl)-18,19,20-trinor-PGF$_{2\alpha}$ methyl ester.

4. A compound according to claim 1 which is 17-oxo-17-(3-chlorophenyl)-18,19,20-trinor-PGF$_{2\alpha}$ methyl ester.

5. A compound according to claim 1 which is 17-oxo-17-(4-chlorophenyl)-18,19,20-trinor-PGF$_{2\alpha}$.

6. A compound according to claim 1 which is 17-oxo-17-(3-chlorophenyl)-18,19,20-trinor-PGF$_{2\alpha}$.

* * * * *